(12) United States Patent
Nagnath

(10) Patent No.: US 8,173,391 B2
(45) Date of Patent: May 8, 2012

(54) GOLDEN YELLOW ALGAE AND METHOD OF PRODUCING THE SAME

(75) Inventor: Baburao Kumble Nagnath, Maharashtra (IN)

(73) Assignee: Choudhary Vidhi, West Bengal (IN)

( * ) Notice: Subject to any disclaimer, the term of this patent is extended or adjusted under 35 U.S.C. 154(b) by 272 days.

(21) Appl. No.: 12/665,116

(22) PCT Filed: Jun. 17, 2008

(86) PCT No.: PCT/IN2008/000394
§ 371 (c)(1),
(2), (4) Date: Mar. 11, 2010

(87) PCT Pub. No.: WO2008/155781
PCT Pub. Date: Dec. 24, 2008

(65) Prior Publication Data
US 2010/0184194 A1    Jul. 22, 2010

(30) Foreign Application Priority Data
Jun. 18, 2007   (IN) ................... 1657/KOL/2007

(51) Int. Cl.
*C12P 23/00*   (2006.01)
*C12N 1/12*   (2006.01)

(52) U.S. Cl. .................. 435/67; 435/257.1; 47/1.4

(58) Field of Classification Search ............ 435/67, 435/257.1; 47/1.4
See application file for complete search history.

(56) References Cited

U.S. PATENT DOCUMENTS

| | | | |
|---|---|---|---|
| 5,437,997 A | 8/1995 | Liao et al. | |
| 5,643,585 A * | 7/1997 | Arad et al. | 424/401 |
| 5,910,254 A * | 6/1999 | Guelcher et al. | 210/703 |

OTHER PUBLICATIONS

Translation of EP 329754 (Oct. 27, 1993) downloaded from the European patent Office Jan. 21, 2012.*
Abd El-Baky, "Spirulina species as a source of carotenoids and alpha-tocopherol and its anticarcinoma factors," Biotechnology, vol. 2, No. 3, 222-240, 2003, entire article esp: abstract; p. 225, p. 223, p. 224, Table 1,2.
Andersen, "Algal Culturing Techniques" Academic Press, 2005, entire book esp: p. 195, col. 2; p. 474, col. 1; p. 129, col. 1,2; p. 206, col. 1; p. 209, col. 2; p. 210, col. 1, Boston, MA.

* cited by examiner

*Primary Examiner* — Susan Hanley
(74) *Attorney, Agent, or Firm* — Kilpatrick Townsend & Stockton LLP

(57) ABSTRACT

The present invention relates to a method for cultivating carotenoid rich golden yellow algae by varying the ratio of carbon to nitrogen content in the culture medium during cultivation and supplementing the media periodically with citrate and acetate compounds to enhance the carotenoid production and produce change in the colour of blue-green algae to golden yellow.

45 Claims, 1 Drawing Sheet

GOLDEN YELLOW ALGAE AND METHOD OF PRODUCING THE SAME

FIELD OF THE INVENTION

The present invention relates to production of carotenoid rich algae and algal biomass.

BACKGROUND OF THE INVENTION

Algae are simple plant-like living organisms. They are unicellular or multicellular living organisms. Algae are found in nature and are divided into different classes and are found in variety of colours and forms. Owing to their high nutritional value, declining food sources, constantly rising population and decreasing agriculture land, algae are considered as potential food for future. Besides nutritional components, algae particularly microalgae are also a major source of valuable additives, other compounds and pigments with therapeutic, chemo-preventive nature and industrial applications.

Carotenoids are class of such pigments having an array of applications which include health food products, cosmetics, feed additives for poultry, livestock, fishes, crustaceans, therapeutic and chemo-preventive supplements in pharmaceuticals and also as colouring agent in various industries. The nutraceutical boom has also added to the demand of mixed carotenoids mainly on the claim of their proven antioxidant and therapeutic properties. Such and other recently discovered health benefits have furthered the market potential of carotenoids. The growing worldwide market value of carotenoids is projected to reach over US$1,000 million in near future. Consumers' demand for natural products favours development of carotenoids from biological sources rather than from synthetic routes due to the problem of toxicity.

Many studies have revealed that natural mixed carotenoids have better synergistic effect and provide more antioxidant protection than individual carotenoid components. This has led to increased interest to obtain natural mixed carotenoids rather than individual carotenoid fractions. Natural mixed carotenoids can be obtained from the biological sources including plant material or microalgae. However, productivity and percentage of carotenoid synthesis in plants is relatively low, as a result, the carotenoids produced from plants are more expensive. Several microalgae including blue-green algae are found to contain carotenoids and there has been increased interest to exploit them to produce natural mixed carotenoids.

*Spirulina* is a primitive form of prokaryotic blue-green microalgae belonging to division (phylum) cyanobacteria. *Spirulina* species are photosynthetic, filamentous, rod to spiral-shaped. The most important species are *Spirulina maxima, Spirulina fusiformis, Spirulina pacifica, Spirulina platensis* and many more. *Spirulina* is a valuable source for natural bioactive and nutritional constituents possessing diverse biological activities and nutritional significance. The recent studies also have indicated the antioxidant and immunostimulatory activity of *Spirulina* is attributed to its mixed carotenoids and polysaccharide fractions.

The chemical composition of *Spirulina* includes proteins 55000-72000 mg per 100 gm, carbohydrates 15000-25000 mg per 100 gm, fats (lipids) 6000-8000 mg per 100 gm, along with vitamins 350-650 mg per 100 gm, minerals 5000-7000 mg per 100 gm, pigments like natural mixed carotenoids 370 mg per 100 gm, chlorophyll-a 1000 mg per 100 gm and phycocyanin 14000 mg per 100 gm. The natural mixed carotenoid fraction of the *Spirulina* is reported to consist of beta-carotenes, zeaxanthene, echinenone, beta-cryptoxanthene, hydroxyechinenone, and other carotenoids. There has been an increasing demand world over for growing *Spirulina* for its end application in food and feed supplements, nutraceuticals and cosmetics. However, its intense blue-green colour and other organoleptic characteristics such as taste and flavour are also not so pleasant, limits its major commercial applications.

There have been many culture protocols, which have been proposed to produce conventionally available *Spirulina*.

CN121883 relates to the growth and propagation of blue-green algae. It discloses a method for regulating and controlling carbon source and pH value in cultivating *Spirulina*. NaHCO3 or carbon dioxide is added to the culture medium for precise control of pH so as to promote the growth and propagation of blue-green algae.

CN1254012 relates to cultivating edible fresh *Spirulina*, in inorganic compounds containing NaHCO3 with a pH of 8-11 and water temperature of 25-40 deg C.

RO117388 discloses a mutant of *Spirulina platensis* grown in continuous flow cultivation with medium possessing NaHCO3, NaNO3 and other inorganic nutrients.

JP1037281 reflects a culture method for marine blue-green algae with steps of adding condensed phosphate at specific dosages to the culture solution, dissociating ample iron ion, and maintaining a dissolution state to promote their growths. As described above, Na2CO3, NaHCO3, NaH2PO4 and other inorganic salts are added as nutrients. pH adjuster or buffer is added to obtain the desired pH level suitable for algae growth.

AU2004322412 reflects process for biomass generation of *Spirulina* at pH of 6.5 and 8.0 with bicarbonate of sodium in the range of 1.2 to 3.0% w/v, nitrogen content in the range 0.1 to 0.3% w/v, phosphorus in the range 0.1 to 0.3% w/v and potassium in the range 0.1 to 0.3% w/v in a sea water based medium.

The patent documents as mentioned above only reveal nutrient inputs and steps for obtaining higher biomass of *Spirulina*.

There have been even attempts to propose protocols to selectively increase some of the nutritional components such as iron, selenium, geranium or others.

CN1144844 relates to manufacture of iron rich *Spirulina* with ferrous methionine usage.

CN1092104 discloses cultivation of *Spirulina* in geranium dioxide and sodium selenite to produce *Spirulina* containing geranium and selenium.

However, so far there have not been any successful attempts to grow *Spirulina* or other microalgae including blue-green algae with increased natural mixed carotenoids contents with significantly high amounts. Besides, there have been no significant efforts focused on producing *Spirulina* with visually agreeable appearance and improved organoleptic characteristics.

Thus, there is an unmet demand to cultivate microalgae including *Spirulina* and other blue-green algae with increased contents of natural mixed carotenoids, with visually agreeable appearance and organoleptic characteristics.

SUMMARY OF THE INVENTION

It is an object of the present invention to provide a method for cultivating carotenoid and biomass rich algae.

It is also an object of the present invention to provide for cartotenoid and carbohydrate rich algal biomass.

According to one embodiment of the present invention, there is provided a method for cultivating carotenoid rich golden yellow algae comprising the steps of culturing an algae in a medium containing low carbon concentration and moderate nitrogen concentration initially for 5 to 7 days. Increasing the concentration of carbon and reducing nitrogen concentration thereafter and cultivating the algae for another 5 to 7 days. After increasing the concentration of carbon source, the culture media is periodically supplemented with a high carbon organic nutrient. The culture is harvested thereafter to obtain carotenoid rich algae having golden yellow colour.

The algae used for culturing is selected from any genus of the blue green algae. Varying the ratio of carbon to nitrogen content in the culture medium during cultivation and supplementing the media periodically with citrate and acetate compounds enhances the carotenoid production and produces change in the colour of blue-green algae to golden yellow.

Another embodiment of the present invention provides for a carotenoid rich golden yellow algae cultivated by culturing the said algae in a medium containing low carbon and high nitrogen initially for 5 to 7 days. Increasing the concentration of carbon and reducing nitrogen concentration thereafter and cultivating the algae for another 5 to 7 days. After increasing the concentration of carbon source, the culture media is periodically supplemented with a high carbon organic nutrient. The culture is harvested thereafter to obtain carotenoid rich golden yellow algae wherein the carotenoid content of the said algae is at least 600 mg per 100 gm of dry cell mass. In further embodiments of the invention, the algae obtained contains between 600 mg to 1200 mg per 100 gm of dry cell mass.

A further embodiment of the invention provides for a method for producing carotenoids rich algal biomass comprising the steps of culturing an algae in a medium containing low carbon concentration and moderate nitrogen concentration initially for 5 to 7 days. Increasing the concentration of carbon and reducing nitrogen concentration thereafter and cultivating the algae for another 5 to 7 days. After increasing the concentration of carbon source, the culture media is periodically supplemented with a high carbon organic nutrient. The culture is harvested thereafter to obtain carotenoid rich algal biomass.

Another embodiment of the present invention provides for a carotenoid rich algal biomass produced by culturing the said algae in a medium containing low carbon and high nitrogen initially for 5 to 7 days. Increasing the concentration of carbon and reducing nitrogen concentration thereafter and cultivating the algae for another 5 to 7 days. After increasing the concentration of carbon source, the culture media is periodically supplemented with a high carbon organic nutrient. The culture is harvested thereafter to obtain carotenoid rich algal biomass wherein the carotenoid content of the said biomass is at least 600 mg per 100 gm of dry cell mass. In further embodiments of the invention, the algal biomass obtained contains between 600 mg to 1200 mg per 100 gm of dry cell mass.

In the present invention the term "low carbon and moderate nitrogen medium" as used herein refers to a nutrient culturing medium either in liquid, or semisolid form comprising carbon sources at concentrations of 0.1 to 0.15 g/l; and nitrogen source at a concentration of 0.06 to 0.35 g/l; along with other nutrient components.

DETAILED DESCRIPTION OF THE DRAWINGS

FIG. 1 illustrates golden yellow algae as produced by the method according to an embodiment of the present invention.

DETAILED DESCRIPTION OF THE PREFERRED EMBODIMENTS

While the present invention has been described herein with respect to the various exemplary embodiments, it will be apparent to one of the ordinary skill in the art that many modifications, improvements and sub combinations of the various embodiments, adaptations and variations can be made to the invention without departing from the spirit and the scope thereof.

One embodiment of the present invention provides for a method for cultivating carotenoid rich golden yellow algae comprising the steps of culturing an algae in a medium containing 0.1 to 0.15 g/l carbon source and 0.06 to 0.35 g/l nitrogen source for 5 to 7 days or until the algae develops a yellow tinge. This leads to the growth of the algae up to a desired level. The concentrations of chlorophyll and phycocyanin are lessened. After growing the algae initially in a low carbon and moderate nitrogen medium, the concentration of carbon source is increased to 0.2 to 1.5 g/l while the concentration of nitrogen source is decreased to 0.005 to 0.03 g/l in the culture medium. The algal culture is then allowed to grow for another 5 to 7 days. During this period, the culture medium is periodically supplemented with a high carbon organic nutrient in the form of a citrate or acetate compound or a combination thereof to enhance the carotenoid production and increase the biomass. After 12 to 15 days, the algal culture is harvested to obtained carotenoid rich golden yellow algae in the form of algal biomass.

The carotenoid rich golden yellow algae of the present invention can be obtained by cultivating any algae, which is capable of producing carotenoids. Preferably, the carotenoid rich golden yellow alga in the present invention is produced by cultivating blue green algae like *Oscillatoria, Spirulina, Nostoc, Phormidium, Aphinozemanon-flos-aquae* and *Anabaena*. In one embodiment, the algae used is selected from the genus *Spirulina*. In a further embodiment, the *Spirulina* used is *S. platensis*

The inventor of the present invention has observed that by varying the ratio of carbon to nitrogen content in the culture medium during cultivation and supplementing the media periodically with a high carbon organic compound enhances the carotenoid production by 2 to 3 times. It also lead to reductions in the level of chlorophyll and phycocyanin and produced a change in the colour of blue-green algae to golden yellow.

The blue green algae that may be employed in the present invention to produce carotenoid rich algae are microscopic in nature belonging to the phylum cyanophyta. In the preferred embodiments, the microscopic blue green algae used in the present invention may be selected from those belonging to but without limiting to, genus *Spirulina (Arthrospira), Oscillatoria, Nostoc, Phormidium, Aphinozemanon-flos-aquae* and *Anabaena*.

In one embodiment carotenoid rich algae produced as per the present invention is *Spirulina*. *Spirulina* cultivated as per the present invention may be selected from *Spirulina* species *S. platensis, S. maxima, S. fusiformis, S. pacifica, S. indica, S. massartii, S. jenneri* and *S. subsalsa*. Preferably in the present invention the carotenoid rich *Spirulina* cultivated is *Spirulina platensis*.

Inoculum is prepared by obtaining desired species of the blue green algae either from the natural habitat or from the depository or seed bank institutions and culturing the said algae on an appropriate basal nutrient medium under optimum culture conditions, to obtain desired biomass for using in culture method of the present invention.

In one embodiment, the inoculum is prepared from *Spirulina* species *S. platensis*. The culture of the said algae is grown in a serially diluted 50% strength of traditional Zarrouk's medium with or without 1.5% agar in 250 ml culturing vessel with pH range of about 8.60-10.60, light intensity 02-10 Klux with a light and dark phase of 12 hours each and with agitation every 2 hours interval to enhance the photosynthetic efficiency and accelerate culture growth of alga.

The innoculum is then transferred to a conventionally used culture medium for large-scale production of blue green algae. The carbon and nitrogen concentration of the medium is adjusted 0.1 to 0.15 g/l and 0.06 to 0.35 g/l respectively and the algae is allowed to grow for 5 to 7 days or until the algae starts to develop a yellow tinge. As it would be evident to a person skilled in the art of cultivating algae on a large scale, the culture medium can be prepared in fresh water or salt water.

After 5 to 7 days, the concentration of carbon and nitrogen in the medium is adjusted to 0.2 to 1.5 g/l and 0.005 to 0.03 g/l respectively and the algae is further allowed to grow for another 5 to 7 days. During this period, the culture medium is supplemented periodically with a high carbon organic nutrient in the form of a citrate or acetate compound or a combination thereof, to enhance the production of biomass and carotenoid in the algal cells.

In one embodiment the medium is supplemented with citrate compounds selected from ferric citrate or sodium citrate. In another embodiment, the medium is supplemented with acetate compounds selected from potassium or sodium acetate. Concentration of citrate and acetate compounds used in the present invention is given in table 1

TABLE 1

| S. No | Salts | mg/Liter |
| --- | --- | --- |
| 1 | Ferric or Sodium citrate | 05-10 |
| 2 | Potassium or Sodium acetate | 75-250 |

There is no particular limitation to the culture system that may be used in the present invention for producing carotenoid rich algae as long as the culture system is capable of supporting the growth and photosynthetic efficiency of the algae. At small scale the culture system that may comprise of tubes, bottles, flasks, carboys, bucket, tub, tanks, bioreactors of various types or open or green house or glass house race way ponds of the capacity ranging from 50 ml to 1000 liters. At a large scale the culture system may be selected from open or closed cylindrical containers, tanks, bioreactors of various types or open or green house or glass house raceway ponds. The culture system as mentioned above can be fitted with aeration, agitation, light and temperature controlling devices.

The culture medium is further supplied with nutrients constituents selected from but not limiting to dipotassium hydrogen phosphate, potassium sulphate, magnesium sulphate, calcium chloride, ferrous sulphate, A 5 elements such as Mn, Zn, Co, Cu, Mo, sodium chloride etc which may be required for the growth of algae as is known to a person skilled in the art.

According to one preferred embodiment of the present invention, the low carbon and moderate nitrogen containing media is describe in table 2:

TABLE 2

| S. No | Salts | mg/Liter |
| --- | --- | --- |
| 1. | Di potassium hydrogen phosphate | 50-200 |
| 2. | Sodium nitrate or Ammonium sulphate | 175-350 60-120 |
| 3. | Potassium sulphate | 75-500 |
| 4. | Magnesium sulphate | 200-350 |
| 5. | Calcium chloride | 20-50 |
| 6. | Ferrous sulphate | 10-25 |

TABLE 2-continued

| S. No | Salts | mg/Liter |
| --- | --- | --- |
| 7. | Sodium bicarbonate or Sodium carbonate | 100-150 |
| 8. | A 5 elements (Mn, Zn, Co, Cu, and Mo) | Traces |
| 9. | Sodium chloride (crude) | 600-6000 |

The medium as per the present invention may be prepared by using either fresh water or seawater or combination thereof.

As per an embodiment of the present invention, the Carbon source employed in the present invention is selected from sodium carbonate or sodium bicarbonate or a combination thereof.

As per further embodiment of the present invention, the nitrogen source employed in the present invention is selected from sodium nitrate or ammonium sulphate. However, other nitrogen sources which support growth of blue green algae can also be employed for the purpose of present invention.

According to one preferred embodiment of the present invention, the high carbon and low nitrogen containing media is describe in table 3:

TABLE 3

| S. No | Salts | mg/Liter |
| --- | --- | --- |
| 1. | Di potassium hydrogen phosphate | 50-200 |
| 2. | Sodium nitrate or Ammonium sulphate | 15-30 5-15 |
| 3. | Potassium sulphate | 75-500 |
| 4. | Magnesium sulphate | 200-350 |
| 5. | Calcium chloride | 20-50 |
| 6. | Ferrous sulphate | 10-25 |
| 7. | Sodium bicarbonate or Sodium carbonate | 200-1500 |
| 8. | A 5 elements (Mn, Zn, Co, Cu, and Mo) | Traces |
| 9. | Sodium chloride (crude) | 600-6000 |

During the entire culture process the temperature of the algal culture is maintained between the range of 6 to 36 degree centigrade, According to preferred embodiment, the temperature is maintained preferably in the range of 26 to 30 degree centigrade. The culture is subjected to light irradiation of about 1-100 Kilo lux, preferably in the range of 40 to 60 Kilo lux. The pH of the culture is maintained in the range of 7.8 to 10.8, it is maintained preferably in the range of 9.2 to 9.6 by aeration with $CO_2$. To liberate the evolved oxygen, facilitate optimum nutrient uptake and to subject the culture to optimum light the culture is agitated manually or mechanically at 5 rpm or more, preferably at 12-16 rpm. The depth of the culture system is kept at 5 cm or more, preferably 12 to 16 cm, to influx a positive influence on the growth of the algal biomass for obtaining higher yield of carotenoids.

The method can be performed either in batch mode or in continuous phase by repeating the above pattern of culturing in low carbon moderate nitrogen medium, followed by adding high carbon low nitrogen medium and further supplementing periodically with citrate and acetate compounds.

The carotenoid rich algae is harvested employing any conventional means preferably by passing on 100-150-mesh nylon screen or cloth. The pH of the harvested carotenoid rich *Spirulina* biomass ranges from 9.6 to 10.8. In order to reduce the pH of the carotenoid rich algae, the biomass is washed with ample water; preferably acidic water to wash out adhered salts and brings pH to neutral or around 7.0.

Depending upon the end use, the algae may be converted into a dry form by subjecting the wet biomass to drying by suitable means such as sun drying, spray drying, oven drying, drum drying, hot air drying or freeze drying.

The carotenoid rich algae or the biomass obtained using the present invention, either in wet or dry form can be packaged preferably under vacuum or sparged with nitrogen gas in a suitable packaging material impermeable to light, air and moisture and can be stored at temperature of about 4-28 degree centigrade.

The algae obtained using the present invention comprises at least 600 mg of mixed carotenoids per 100 gm of dry cell biomass or more. The carotenoid rich algae of the preset invention in addition to the increase in the mixed carotenoid levels also has a profound increase in carbohydrates content. in the range of 40000-60000 mg per 100 gm of dry cell biomass.

The algae cultivated using the method of the present invention has mixed carotenoids levels as high as 2 to 3 times more than that of the naturally occurring or conventionally cultivated algae and serves as an efficient source of natural mixed carotenoids. The reduction is chlorophyll and phycocyanin levels improves visually appearance and organoleptic characteristics of the algae as compared to the naturally occurring and conventionally cultivated blue green algae having unappealing appearance and organoleptic characteristics. This further, expands its scope of utilization in the fields of food and feed supplements, nutraceuticals, cosmetics and other industrial applications. While the present invention has been described herein with respect to the various exemplary embodiments, it will be apparent to one of the ordinary skill in the art that many modifications, improvements and sub combinations of the various embodiments, adaptations and variations can be made to the invention without departing from the spirit and the scope thereof.

EXAMPLES

Example 1

Carotenoid Rich Golden Yellow *Spirulina platensis*:

To obtain the carotenoid rich *Spirulina platensis*, was used for inoculum preparation. The inoculum was prepared under sterile conditions by culturing *Spirulina platensis* trichomes in 50% strength Zarrouk's medium with 0.75-1.5% agar having pH 9.5 under a light regime of 12:12 hrs dark and light phases at 2-10 Klux light intensity, at a temperature of 28 to 32° C. The inoculum thus obtained was further grown in 50% strength of Zarrouk's medium with initial pH of 9 to 9.5 and under light intensity of 2-10 Klux with a light and dark phase of 12 hours with frequent agitations for uniform mixing of the culture nutrients for better photosynthetic efficiency and attaining sufficient built up of the inoculum.

The above *Spirulina* was used as an innoculum for the present invention. 20 liter of *Spirulina platensis* inoculum was cultured in a 2×2 pond having a depth of 12-16 cm for the duration of about 5 to 7 days in a low carbon and moderate nitrogen medium comprising of the constituents as described herein below:

| S. NO | Inorganic salts | mg/liter |
|---|---|---|
| 1. | Di potassium hydrogen phosphate | 50 |
| 2. | Sodium nitrate | 300 |
| 3. | Potassium sulphate | 75 |
| 4. | Magnesium sulphate | 200 |
| 5. | Calcium chloride | 20 |

-continued

| S. NO | Inorganic salts | mg/liter |
|---|---|---|
| 6. | Ferrous sulphate | 10 |
| 7. | Sodium bicarbonate | 150 |
| 8. | A 5 elements (Mn, Zn, Co, Cu, and Mo) | Traces |
| 9. | Sodium chloride (crude) | 600 |

The low carbon and moderate nitrogen culture medium was supplemented at an interval of about 2-3 days. The culture was allowed to grow at a temperature in the range of 26-36° C., light intensity of 10-80 Klux and agitation at regular time interval of approximately 1-2 hours during light phase. At the end of the culturing duration of said 5 to 7 days the *Spirulina* trichomes appeared long, semi-buoyant with visible mucilaginous secretion, were dull brownish green with profound yellowish tinge.

The carbon and nitrogen concentration was then increased to allow *Spirulina platensis* culture as grown above in the high carbon and low nitrogen medium comprising following constituents for a period of about 5 to 7 days comprising:

| S. No | Salts | mg/Liter |
|---|---|---|
| 1. | Di potassium hydrogen phosphate | 50 |
| 2. | Sodium nitrate | 15 |
| 3. | Potassium sulphate | 75 |
| 4. | Magnesium sulphate | 200 |
| 5. | Calcium chloride | 20 |
| 6. | Ferrous sulphate | 10 |
| 7. | Sodium bicarbonate | 1500 |
| 8. | A 5 elements (Mn, Zn, Co, Cu, and Mo) | Traces |
| 9. | Sodium chloride (crude) | 600 |

The temperature of the culturing medium was maintained in the range of 16-36 deg C. The culture was allowed to grow in 1-100 Klux light intensity. After growing in the high carbon and low nitrogen medium the *Spirulina platensis* trichomes appeared long, least buoyant with visible mucilaginous secretion and golden yellow in colour.

The above *Spirulina* culture was further periodically supplemented with citrate and acetate compounds as describe below

| S. No | Salts | mg/Liter |
|---|---|---|
| 1 | Ferric citrate | 05 |
| 2 | Sodium acetate | 150 |

The pH of the culture was adjusted by passing the $CO_2$ gas at 5% level in bubbled air. The temperature was maintained in the range of 16-36° C. The light intensity was 10-80 Klux. The alga culture was subjected to frequent agitations. The *Spirulina* trichomes appear long and least buoyant with mucilaginous secretion. The algal culture attained rich golden yellow colour.

The biomass of carotenoid rich golden yellow *Spirulina* obtained was about 0.75 g/l. The *Spirulina* comprised natural mixed carotenoids 880 mg per 100 gm of dry cell biomass.

The carotenoid rich golden yellow *Spirulina* in addition to the increase in the mixed carotenoid levels also showed profound increase in carbohydrates content with 43600 mg per 100 gm of dry cell biomass.

The invention claimed is:

1. A method for cultivating carotenoid-rich golden yellow algae comprising the steps of:
   (a) culturing an algae in a culture medium containing 0.1 to 0.15 g/l of a carbon source and 0.06 to 0.35 g/l of a nitrogen source for 5 to 7 days;
   (b) after completion of step (a), adjusting the concentration of the carbon source in the culture medium to 0.2 to 1.5 g/l and the concentration of the nitrogen source in the culture medium to 0.005 to 0.03 g/l to obtain an adjusted culture medium and cultivating the algae resulting from (a) in the adjusted culture medium for another 5 to 7 days;
   (c) periodically supplementing the adjusted culture medium in step (b) with a high carbon organic nutrient; and
   (d) harvesting carotenoid-rich golden yellow algae resulting from step (c).

2. The method of claim 1 wherein the algae cultivated in step (a) is selected from the genera *Spirulina, Oscillaloria, Nostoc, Phormidium, Aphinozemanon-flos-aque* and *Anabaena*.

3. The method of claim 2 wherein the *Spirulina* is selected from *S. platensis, S. maxima, S. fusiformis, S. pacifica, S. indica. S. massartii, S. jenneri* and *S. subsala*.

4. The method of claim 3 wherein the *Spirulina* is *S. platensis*.

5. The method of claim 1 wherein the carbon source is selected from sodium carbonate, sodium biocarbonate or a combination thereof.

6. The method of claim 1 wherein the nitrogen source is selected from sodium nitrate, ammonium sulphate or a combination thereof.

7. The method of claim 1 wherein the high carbon organic nutrient is selected from a citrate compound, an acetate compound or a combination thereof.

8. The method of claim 7 wherein citrate compound is ferric citrate in the range of 5 mg/l to 10 mg/l.

9. The method of claim 7 wherein citrate compound is sodium citrate in the range of 5 mg/l to 10 mg/l.

10. The method of claim 7 wherein the acetate compound is potassium acetate in the range of 75 mg/l to 250 mg/l.

11. The method of claim 7 wherein the acetate compound is sodium acetate in the range of 75 mg/l to 250 mg/l.

12. The method of claim 1 wherein the culture medium of step (a) or (b) further comprises dipotassium hydrogen phosphate, potassium sulphate, magnesium sulphate, calcium chloride, ferrous sulphate, sodium chloride, and salts of Mn, Zn, Co, Cu and Mo.

13. The method of claim 1 wherein the steps (a), (b) and (c) are carried out at a temperature in the range of 6 to 36° C.

14. The method of claim 1 wherein the steps (a), (b) and (c) are carried out at light intensity in the range of 1 to 100 Klux.

15. The method of claim 1, wherein steps (a), (b) and (c) are carried out at a pH in the range of 8.2 to 10.8.

16. The method of claim 1 wherein the culture medium has a depth of at least 5 cm.

17. A carotenoid rich-golden yellow algae produced by the method of claim 1 wherein the carotenoid rich-golden yellow algae contains at least 600 mg mixed carotenoids per 100 gm of dry cell mass.

18. The carotenoid rich-golden yellow algae of claim 17 wherein the carotenoid rich-golden yellow algae contains mixed carotenoids in the range of 600 mg to 1200 mg per 100 gm of dry cell mass.

19. The carotenoid-rich golden yellow algae of claim 17 further having a carbohydrate content of 40000-60000 mg per 100 gm of dry cell mass.

20. The carotenoid-rich golden yellow algae of claim 17 wherein the carotenoid-rich yellow algae has been cultivated from algae capable of producing mixed carotenoids.

21. The carotenoid-rich golden yellow algae of claim 17 wherein the carotenoid-rich golden yellow algae has been cultivated from blue green algae selected from the genera *Spirulina, Oscillaloria, Nostoc, Phormidium, Aphinozemanon-flos-aquae* and *Anabaena*.

22. The carotenoid-rich golden yellow algae of claim 21 wherein the blue green algae from the genus *Spirulina* is selected from *S. platensis, S. maxima, S. fusiformis, S. pacifica, S. indica. S. massartii, S. jenneri* and *S. subsala*.

23. The carotenoid-rich golden yellow algae of claim 22 wherein the blue green algae is *Spirulina platensis*.

24. A method for producing carotenoid-rich algal biomass comprising the steps of:
   (a) culturing an algae in a culture medium containing 0.1 to 0.15 g/l of a carbon source and 0.06 to 0.35 g/l of a nitrogen source for 5 to 7 days;
   (b) after the completion of step (a), adjusting the concentration of carbon source in the culture medium to 0.2 to 1.5 g/l and the concentration of nitrogen source in the culture medium to 0.005 to 0.03 g/l to obtain an adjusted culture medium and cultivating the algae resulting from (a) in the adjusted culture medium for another 5 to 7 days;
   (c) periodically supplementing the adjusted culture medium in step (b) with a high carbon organic nutrient; and
   (d) harvesting algal biomass resulting from step (c).

25. The method of claim 24 wherein the algae is selected from the genera *Spirulina, Oscillaloria, Nostoc, Phormidium, Aphinozemanon-flos-aquae* and *Anabaena*.

26. The method of claim 25 wherein the algae is *Spirulina* selected from *S. platensis, S. maxima, S. fusiformis, S. pacifica, S. indica. S. massartii, S. jenneri* and *S. subsala*.

27. The method of claim 26 wherein the *Spirulina* is *S. platensis*.

28. The method of claim 24 wherein the carbon source is selected from sodium carbonate or sodium biocarbonate or a combination thereof.

29. The method of claim 24 wherein the nitrogen source is selected from sodium nitrate, ammonium sulphate or a combination thereof.

30. The method of claim 24 wherein the high carbon organic nutrient is selected from a citrate compound, acetate compound or a combination thereof.

31. The method of claim 30 wherein citrate compound is ferric citrate in the range of 5 mg/l to 10 mg/l.

32. The method of claim 30 wherein citrate compound is sodium citrate in the range of 5 mg/l to 10 mg/l 33. The method of claim 30 wherein the acetate compound is potassium acetate in the range of 75 mg/l to 250 mg/l.

34. The method of claim 30 wherein the acetate compound is sodium acetate in the range of 75 mg/l to 250 mg/l.

35. The method of claim 24 wherein the culture medium of step (a) or (b) further comprises dipotassium hydrogen phosphate, potassium sulphate, magnesium sulphate, calcium chloride, ferrous sulphate, sodium chloride and salts of Mn, Zn, Co, Cu and Mo.

36. The method of claim 24 wherein the steps (a), (b) and (c) are carried out at a temperature in the range of 6 to 36° C.

37. The method of claim 24 wherein the steps (a), (b) and (c) are carried out at a light intensity in the range of 1 to 100 Klux.

38. The method of claim 24, wherein steps (a), (b) and (c) are carried out at a pH in the range of 8.2 to 10.8.

39. The method of claim 24 wherein the culture medium has a depth of at least 5 cm.

40. A carotenoid-rich algal biomass produced by the method of claim 24 wherein the algae in the biomass has been cultivated from blue-green algae.

41. The carotenoid-rich algal biomass of claim 40 wherein the algal biomass contains mixed carotenoids in the range of 600 mg to 1200 mg per 100 gm of dry algal cell mass.

42. The carotenoid-rich algal biomass of claim 40 further having a carbohydrate content of 40000-60000 mg per 100 gm of dry algal cell mass.

43. The carotenoid-rich algal biomass of claim 40 wherein the blue green algae is selected from the genera *Spirulina, Oscillaloria, Nostoc, Phormidium, Aphinozemanon-flos-aque* and *Anabaena*.

44. The carotenoid rich-algal biomass of claim 43, wherein the algae is *Spirulina* selected from *S. platensis, S. maxima, S. fusiformis, S. pacifica, S. indica. S. massartii, S. jenneri* and *S. subsala*.

45. The carotenoid-rich algal biomass of claim 44, wherein the algae is *Spirulina platensis*.

* * * * *